(12) United States Patent
Kunz et al.

(10) Patent No.: US 8,129,558 B2
(45) Date of Patent: Mar. 6, 2012

(54) PESTICIDE NAPHTHYLOXY SUBSTITUTED PHENYLAMIDINE DERIVATIVES

(75) Inventors: Klaus Kunz, Düsseldorf (DE); Jörg Greul, Leichlingen (DE); Oliver Guth, Leverkusen (DE); Benoît Hartmann, Sainte Foy-lès-Lyon (FR); Kerstin Ilg, Köln (DE); Wahed Moradi, Monheim an Rhein (DE); Thomas Seitz, Langenfeld (DE); Peter Dahmen, Neuss (DE); Arnd Voerste, Köln (DE); Ulrike Wachendorff-Neumann, Neuwied (DE); Ralf Dunkel, Lyons (FR); Ronald Ebbert, Nürnberg (DE); Eva-Maria Franken, Leichlingen (DE)

(73) Assignee: Bayer Cropscience AG, Monheim (DE)

( * ) Notice: Subject to any disclaimer, the term of this patent is extended or adjusted under 35 U.S.C. 154(b) by 190 days.

(21) Appl. No.: 12/063,654

(22) PCT Filed: Sep. 12, 2006

(86) PCT No.: PCT/EP2006/066292
§ 371 (c)(1),
(2), (4) Date: Jul. 17, 2008

(87) PCT Pub. No.: WO2007/093227
PCT Pub. Date: Aug. 23, 2007

(65) Prior Publication Data
US 2009/0143431 A1 Jun. 4, 2009

(30) Foreign Application Priority Data

Sep. 13, 2005 (EP) .................................... 05356158

(51) Int. Cl.
C07C 251/08 (2006.01)
(52) U.S. Cl. ....................................................... 558/302
(58) Field of Classification Search ................... 558/302
See application file for complete search history.

(56) References Cited

FOREIGN PATENT DOCUMENTS

| EP | 1 570 736 | 9/2005 |
|----|-----------|--------|
| WO | WO 00/46184 | 8/2000 |

OTHER PUBLICATIONS

International Search Report No. PCT/EP2006/066292, dated Dec. 12, 2006, 2 pgs.

*Primary Examiner* — Rebecca Anderson
(74) *Attorney, Agent, or Firm* — Baker Donelson Bearman, Caldwelll & Berkowitz, PC

(57) ABSTRACT

The present invention relates to 2,5-di-substituted-4-naphthyloxy-substituted-phenyl-amidine derivatives of formula (I) wherein the substituents are as in the description, their process of preparation, their use as fungicide or insecticide active agents, particularly in the form of fungicide or insecticide compositions, and methods for the control of phytopathogenic fungi or damaging insects, notably of plants, using these compounds or compositions.

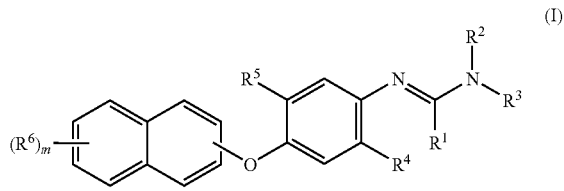

21 Claims, No Drawings

PESTICIDE NAPHTHYLOXY SUBSTITUTED PHENYLAMIDINE DERIVATIVES

CROSS REFERECE TO RELATED APPLICATIONS

This is a §371 National Stage Application of International Application No. PCT/EP2006/066292 filed Sep. 12, 2006, which claims priority from European Application No. 05356158.5 filed Sep. 13, 2005.

BACKGROUND OF THE INVENTION

1. Field of the Invention

The present invention relates to 2,5-di-substituted-2,5-4—naphthyloxy -substituted-phenyl-amidine derivatives, notably to 2,5-dialkyl-4-naphthyloxy-substituted-phenyl-amidine derivatives, their process of preparation, their use as fungicide or insecticide active agents, particularly in the form of fungicide or insecticide compositions, and methods for the control of phytopathogenic fungi or damaging insects, notably of plants, using these compounds or compositions.

2. Description Of Related Art

In international patent application WO-00/46184 certain phenyl-amidine derivatives are disclosed. However, this document does not specifically disclose nor suggest to select such compounds wherein the phenyl ring is substituted according to the invention thus allowing an unexpected and significantly higher fungicide or insecticide activity.

It is always of high-interest in agriculture to use novel pesticide compounds in order to avoid or to control the development of resistant strains to the active ingredients. It is also of high -interest to use novel compounds being more active than those already known, with the aim of decreasing the amounts of active compound to be used, whilst at the same time maintaining an effectiveness at least equivalent to the already known compounds.

In the same way, it is also always of high-interest to use novel insecticide, namatocide or acaricide agents to control damaging insects or other damaging organisms.

We have now found a new family of compounds which possess the above mentioned effects or advantages.

SUMMARY OF THE INVENTION

Accordingly, the present invention provides 2,5-disubstituted-4—naphthyloxy -substituted-phenyl-amidine derivatives of formula (I):

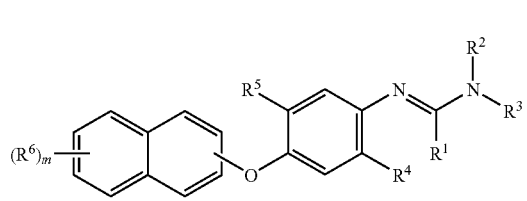

(I)

wherein
- $R^1$ represents H, a substituted or non substituted $C_1$-$C_{12}$-alkyl, a substituted or non substituted $C_2$-$C_{12}$-alkenyl, a substituted or non substituted $C_2$-$C_{12}$-alkynyl, SH or a substituted or non substituted S—$C_1$-$C_{12}$-alkyl;
- $R^2$ represents a substituted or non substituted $C_1$-$C_{12}$-alkyl;
- $R^3$ represents a substituted or non substituted $C_2$-$C_{12}$-alkyl, substituted or non substituted $C_3$-$C_6$-cycloalkyl, substituted or non substituted $C_2$-$C_{12}$-alkenyl, substituted or non substituted $C_2$-$C_{12}$-alkynyl, halogeno-$C_1$-$C_{12}$-alkyl; or
- $R^1$ and $R^2$, $R^1$ and $R^3$ or $R^2$ and $R^3$ can form together a substituted or non substituted 5 to 7-membered heterocycle;
- $R^4$ represents a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;
- $R^5$ represents H, a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;
- $R^6$ represents H, halogen, CN, substituted or non substituted phenoxy, substituted or non substituted $C_1$-$C_{12}$-alkyl, halogeno-$C_1$-$C_{12}$-alkyl, $OR^7$, $SR^7$, trialkyl-silyl, $COR^7$, $COOR^7$, $C(R^7)$=$NOR^7$; $NR^7R^8$, $CONR^7R^8$, $SO_2NR^7R^8$, $SONR^7R^8$;
- $R^7$, $R^8$ represent independently H, substituted or non substituted $C_1$-$C_2$-alkyl, aryl or $R^7$ and $R^8$ can form a substituted or non substituted, saturated or non saturated 5 to 7-membered heterocycle including one or more atoms selected in the list consisting of O, N and S;
- m represents 1, 2, 3 or 4;

as well as salts; N-oxydes, metallic complexes, metalloidic complexes and optically active isomers thereof.

DETAILED DESCRIPTION OF A PREFERRED EMBODIMENT

Any of the compounds according to the invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compounds according to the invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

For the compounds according to the invention, halogen means either one of fluorine, bromine, chlorine or iodine and heteroatom can be nitrogen, oxygen or sulphur.

Preferred compounds of formula (I) according to the invention are those wherein $R^1$ represents H; $C_1$-$C_{12}$-alkyl, preferably $C_1$-$C_{12}$-alkyl like methyl; or SH.

Other preferred compounds of formula (I) according to the invention are those wherein $R^2$ represents methyl.

Still other preferred compounds of formula (I) according to the invention are those wherein $R^3$ represents $C_2$-$C_{12}$-alkyl, preferably a non substituted $C_2$-$C_4$-alkyl like ethyl, n-propyl, i-propyl; $C_2$-$C_{12}$-alkenyl, preferably $C_3$-$C_4$-alkenyl like propenyl or allyl; $C_3$-$C_6$-cycloalkyl like cyclopropyl.

Still other preferred compounds of formula (I) according to the invention are those wherein $R^2$ and $R^3$ can form together a substituted or non substituted 5 to 7-membered heterocycle, preferably a 6-membered heterocycle, more preferably a pipiridinyl or a pyrrolidinyl, even more preferably a 2-alkylated-pyrrolidinyl like a 2-methyl-pyrrolidinyl.

Still other preferred compounds of formula (I) according to the invention are those wherein $R^4$ represents a $C_1$-$C_{12}$-alkyl, preferably a non substituted $C_1$-$C_{12}$-alkyl like methyl; a halogen atom like a chlorine atom.

Still other preferred compounds of formula (I) according to the invention are those wherein $R^5$ represents a $C_1$-$C_{12}$-alkyl, preferably a non substituted $C_1$-$C_{12}$-alkyl like methyl; a halogen atom like a chlorine atom.

Still other preferred compounds of formula (I) according to the invention are those wherein $R^6$ represents substituted $C_1$-$C_{12}$-alkyl, notably branched $C_1$-$C_{12}$-alkyl like CH(OH)$R^7$ or C($R^7$)=NO$R^8$ wherein $R^7$ and $R^8$ are as herein-described.

The above mentioned preferences with regard to the substituents of the compounds according to the invention can be combined in various manners. These combinations of preferred features thus provide sub-classes of compounds according to the invention. Examples of such sub-classes of preferred compounds according to the invention can combine:

preferred features of $R^1$ with preferred features of $R^2$ to $R^8$;
preferred features of $R^2$ with preferred features of $R^1$ to $R^8$;
preferred features of $R^3$ with preferred features of $R^1$ to $R^8$;
preferred features of $R^4$ with preferred features of $R^1$ to $R^8$;
preferred features of $R^5$ with preferred features of $R^1$ to $R^8$.

In these combinations of preferred features of the substituents of the compounds according to the invention, the said preferred features can also be selected among the more preferred features of each of $R^1$ to $R^8$ and m so as to form most preferred subclasses of compounds according to the invention.

The present invention also relates to a process for the preparation of compounds of formula (I).

Thus according to a further aspect according to the invention, there is provided a process P1 for the preparation of compound of formula (I) and illustrated according to the following reaction scheme:

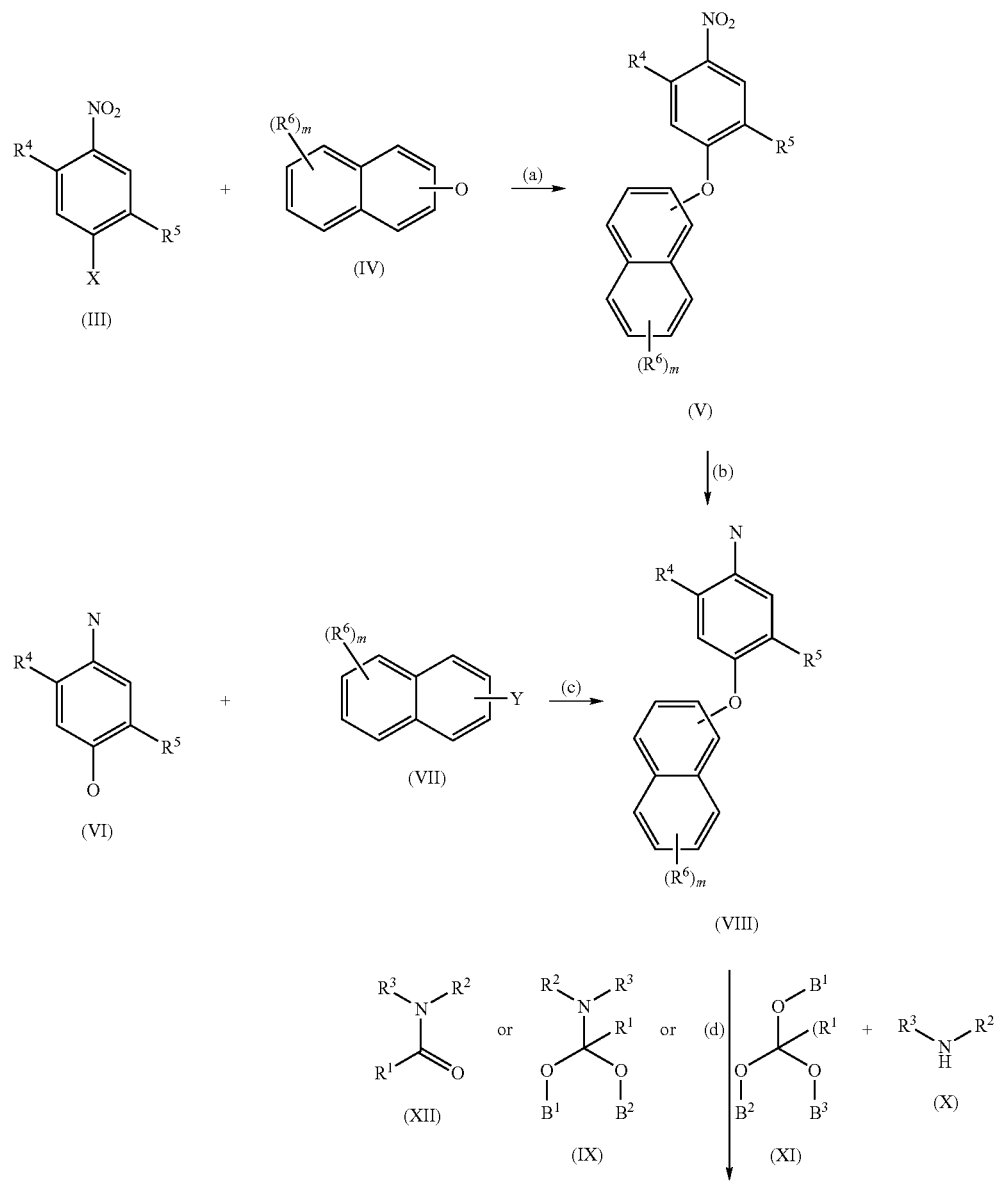

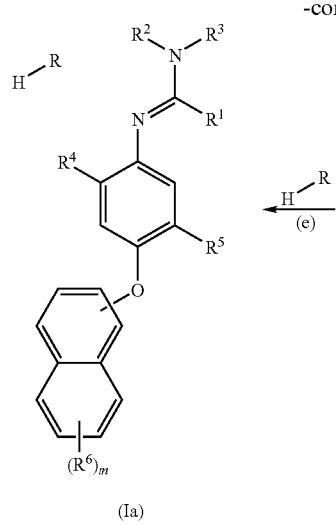

(Ia)

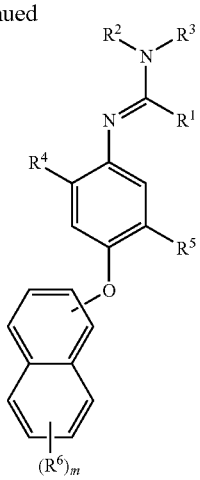

(I)

wherein
$R^4$ to $R^6$ and m are as herein-defined.

Process step (a) according to the invention can further comprise one or more of the following characteristics:
presence of a base;
presence of a diluent;
presence of a catalyst.

Preferred reaction conditions for carrying out process step (b) according to the invention comprise reaction with stannous chloride in concentrated hydrochloric acid.

Aniline derivatives of formula (VIII) can also be prepared according to process step (c) by reacting aniline derivatives of formula (VI)

Aminophenylether derivatives of formula (VIII) can be prepared according to process step (a) by reacting nitrobenzene derivatives of formula (III)

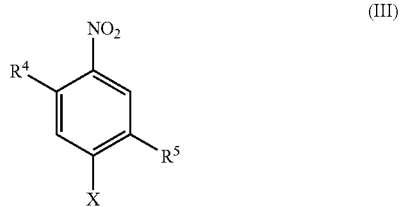

(III)

wherein
$R^4$ and $R^5$ are as herein-defined;
X represents halogen, triflate, SOMe, mesylate or tosylate;
with hydroxynaphthalene derivatives of formula (IV)

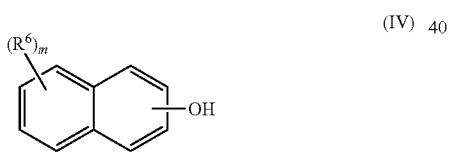

(IV)

wherein
$R^6$ and m are as herein-defined
followed by process step (b) comprising the reduction of nitrophenylether derivatives of formula (v) obtained further to process step (a)

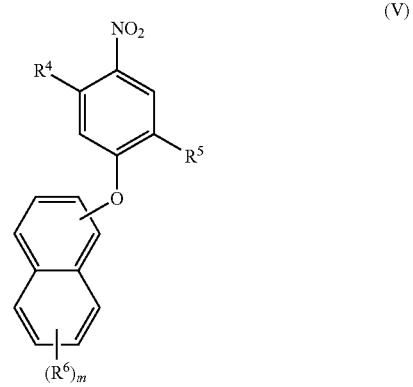

(V)

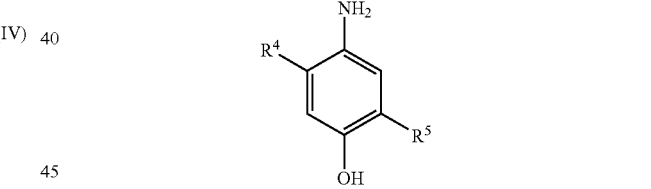

(VI)

wherein
$R^4$ and $R^5$ are as herein-defined;
with naphthalene derivatives of formula (VI)

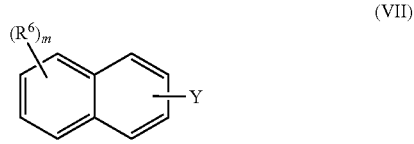

(VII)

wherein
$R^6$ and m are as herein-defined;
Y represents halogen, triflate, SOMe, mesylate or tosylate.

Process step (c) according to the invention can further comprise one or more of the following characteristics:
presence of a base;
presence of a diluent;
presence of a catalyst.

Amidine derivatives of formula (I) can be prepared according to process step (d) by reacting aniline derivatives of formula (VIII)

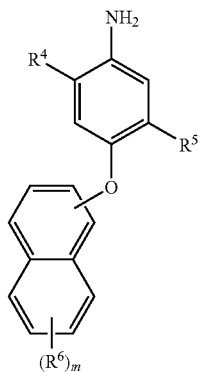

(VIII)

wherein
$R^4$ to $R^6$ and m are as herein-defined.

Amidine derivatives of formula (I) can be obtained by a further process according to the invention. Various alternatives of process (d) according to the invention can be considered, they are defined as process (d1), process (d2) and process (d3) according to the invention.

Process (d) according to the invention comprises reacting aniline derivatives of formulae (VII) with different reagents thus defining processes (d1), (d2) and (d3) respectively Process (d1) is carried out further using amino-acetal derivatives of formula (IX)

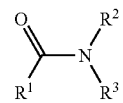

(IX)

wherein
$R^1$ to $R^3$ are as herein-defined
$B^1$ and $B^2$ represent each alkyl or together cycloalkyl.

Process (d1) according to the invention can further comprise one or more of the following c characteristics:
presence of an acid or base;
presence of a diluent.

Process (d2) is carried out further using amine derivatives of formula (X)

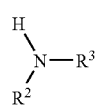

(X)

wherein
$R^2$ and $R^3$ are as herein-defined;
in the presence of orthoester derivatives of formula (XI)

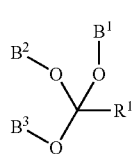

(XI)

wherein
$R^1$ is as herein-defined;
$B^1$ to $B^3$ represent each alkyl.

Process (d3) is carried out further using amide derivatives of formula (XII)

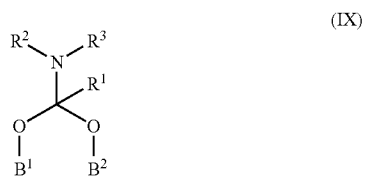

(XII)

wherein
$R^1$ to $R^3$ are as herein-defined.

Process (d3) according to the invention can further comprise one or more of the following characteristics:
presence of a halogenation agent like $PCl_5$, $PCl_3$, $POCl_3$, $SOCl_2$;
presence of a diluent.

Suitable diluents for carrying out the processes (a), (b) and (c) according to the invention are all customary inert organic solvents. Preference is given to using aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorobenzene, dichloromethane, chloroform, carbon tetrachloride, dichloroethane or trichloro-ethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; mixtures thereof with water or pure water.

Suitable diluents for carrying out the processes (d1), (d2) and (d3) according to the invention are in each case all customary inert organic solvents. Preference is given to using aliphatic, alicyclic or aromatic hydrocarbons, such as petroleum ether, hexane, heptane, cyclohexane, methylcyclohexane, benzene, toluene, xylene or decalin; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethyl-acetamide, N-methylformanilide, N-methylpyrrolidone or hexamethylphosphoric triamide; esters, such as methyl acetate or ethyl acetate; sulphoxides, such as dimethylsulphoxide; or sulphones, such as sulpholane; alcohols, such as methanol, ethanol, n- or iso-propanol, n-, iso-,sec- or tert-butanol, ethanediol, propane-1,2-diol, ethoxyethanol, methoxyethanol, diethylene-glycolmonomethylether, diethyleneglycolmonoethylether; mixtures thereof with water or pure water.

Suitable acid binders for carrying out the processes (a), (b) and (c) according to the invention are all inorganic and organic bases customary for such reactions. Preference is given to using alkaline earth metal or alkali metal hydrides, hydroxides, amides, alcoholates, acetates, carbonates or hydrogen carbonates, such as sodium hydride, sodium amide, lithium diisoproylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, or ammonium carbonate; and also tertiary amines, such as trimethylamine, triethylamine, tributylamine, N, N-dimethylaniline, N,N-dimethyl-benzylamine pyridine, N-methylpiperidine, N-methylmorpholine, N,N-dimethylaminopyridine, diazabicyclooctane (DABCO), diazabicyclononene (DBN) or diaza-bicycloundecene (DBU).

Suitable acid binders for carrying out the processes (b), (c), (d) according to the invention are in each case all inorganic and organic bases customary for such reactions. Preference is given to using alkaline earth metal or alkali metal hydrides, hydroxides, amides, alcoholates, acetates, fluorides, phosphates, carbonates or hydrogen carbonates, such as sodium hydride, sodium-amide, lithium diisopropylamide, sodium methanolate, sodium ethanolate, potassium tert-butanolate, sodium hydroxide, potassium hydroxide, sodium acetate, sodium phosphate, potassium phosphate, potassium fluoride, caesium fluoride, sodium carbonate, potassium carbonate, potassium hydrogencarbonate, sodium hydrogencarbonate or caesium carbonate; and also tertiary amines, such as trimethylamine, triethylamine, tributylamine, N,N-dimethylaniline, N, N-dimethyl-benzylamine, pyridine, N-methylpiperidine, N-methylmorpholine, N,N-dimethylamino-pyridine, diazabicyclooctane (DABCO), diazabicyclononene (DBN) or diazabicycloundecene (DBU).

Suitable acids for carrying out the process (d1) according to the invention are all inorganic and organic acids customary for such reactions. Preference is given to using para-toluene sulfonic acid, methane sulfonic acid, hydrochloric acid (gas, aqueous or organic solution) or sulphuric acid.

Suitable condensing agents for carrying out the process (d3) according to the invention are all condensing agents customary for such amidation reactions. Preference is given to using acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyldiimidazole, 2-ethoxy-N-ethoxycarbonyl-1,2-dihydroquinoline (EEDQ), triphenylphosphine/tetrachloromethane or bromo-tripyrrolidino-phosphonium-hexafluorophosphate.

Compounds of formula (I) according to the invention can be prepared according to the herein described processes. It will nevertheless be understood that, on the basis of his general knowledge and of available publications, the skilled worker will be able to adapt these processes according to the specifics of each of the compounds which it is desired to synthesise.

In a further aspect, the present invention also relates to a fungicide or insecticide composition comprising an effective and non-phytotoxic amount of an active compound of formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicide composition according to the invention.

This amount can be determined by systematic field trials, which are within the capabilities of a person skilled in the art.

Thus, according to the invention, there is provided a fungicide or insecticide composition comprising, as an active ingredient, an effective amount of a compound of formula (I) as herein-defined and an agriculturally acceptable support, carrier or filler.

According to the invention, the term "support" denotes a natural or synthetic, organic or inorganic compound with which the active compound of formula (I) is combined or associated to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the present compounds containing sulphate, sulphonate and phosphate functions. The presence of at least one surfactant is generally essential when the active compound and/or the inert support are water-insoluble and when the vector agent for the application is water. Preferably, surfactant content may be comprised from 5% to 40% by weight of the composition.

Optionally, additional components may also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention may contain from 0.05 to 99% by weight of active compound, preferably 10 to 70% by weight.

Compositions according to the invention can be used in various forms such as aerosol dispenser, bait (ready for use), bait concentrate, block bait, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, grain bait, granular bait, granule, hot fogging concentrate, macrogranule, microgranule, oil dispersible powder, oil miscible flowable concentrate, oil miscible liquid, paste, plant rodlet, plate bait, powder for dry seed treatment, scrap bait, seed coated with a pesticide, smoke candle, smoke cartridge, smoke generator, smoke pellet, smoke rodlet, smoke tablet, smoke tin, soluble concentrate, soluble powder, solution for seed treatment, suspension concentrate (=flowable concentrate), tracking powder, ultra low volume (ulv) liquid, ultra low volume (ulv) suspension, vapour releasing product, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity.

The mixtures with other fungicide compounds are particularly advantageous. Examples of suitable fungicide mixing partners may be selected in the following lists:

B1) a compound capable to inhibit the nucleic acid synthesis like benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid;

B2) a compound capable to inhibit the mitosis and cell division like benomyl, carbendazim, diethofencarb, fuberidazole, pencycuron, thiabendazole thiophanate-methyl, zoxamide;

B3) a compound capable to inhibit the respiration for example
as CI-respiration inhibitor like diflumetorim;
as CII-respiration inhibitor like boscalid, carboxin, fenfuram, flutolanil, furametpyr, mepronil, oxycarboxine, penthiopyrad, thifluzamide;
as CIII-respiration inhibitor like azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin;

B4) a compound capable of to act as an uncoupler like dinocap, fluazinam;

B5) a compound capable to inhibit ATP production like fentin acetate, fentin chloride, fentin hydroxide, silthiofam;

B6) a compound capable to inhibit AA and protein biosynthesis like andoprim, blasticidin-S, cyprodinil, kasugamycin, kasugamycin hydrochloride hydrate, mepanipyrim, pyrimethanil;

B7) a compound capable to inhibit the signal transduction like fenpiclonil, fludioxonil, quinoxyfen;

B8) a compound capable to inhibit lipid and membrane synthesis like chlozolinate, iprodione, procymidone, vinclozolin, pyrazophos, edifenphos, iprobenfos (IBP), isoprothiolane, tolclofos-methyl, biphenyl, iodocarb, propamocarb, propamocarb-hydrochloride;

B9) a compound capable to inhibit ergosterol biosynthesis like fenhexamid, azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazol, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine;

B10) a compound capable to inhibit cell wall synthesis like benthiavalicarb, bialaphos, dimethomorph, flumorph, iprovalicarb, polyoxins, polyoxorim, validamycin A;

B11) a compound capable to inhibit melanine biosynthesis like carpropamid, diclocymet, fenoxanil, phtalide, pyroquilon, tricyclazole;

B12) a compound capable to induce a host defence like acibenzolar-5-methyl, probenazole, tiadinil;

B13) a compound capable to have a multisite action like captafol, captan, chlorothalonil, copper preparations such as copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, propineb, sulphur and sulphur preparations including calcium polysulphide, thiram, tolylfluanid, zineb, ziram;

B14) a compound selected in the following list: amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulphate, diphenylamine, ethaboxam, ferimzone, flumetover, flusulfamide, fosetyl-aluminium, fosetyl-calcium, fosetyl-sodium, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, phosphorous acid and its salts, piperalin, propanosine-sodium, proquinazid, pyrroInitrine, quintozene, tecloftalam, tecnazene, triazoxide, trichlamide, zarilamid and 2,3,5,6-tetrachloro-4-(methylsulfonyl)-pyridine, N-(4-chloro-2-nitrophenyl)-N-ethyl-4-methyl-benzenesulfonamide, 2-amino-4-methyl-N-phenyl-5-thiazolecarboxamide, 2-chloro-N-(2, 3-dihydro-1,3-trimethyl-1H-inden-4-yl)-3-pyridincarboxamide, 3-[5-(4-chlorophenyl)-2,3-dimethylisoxazolidin-3-yl]pyridine, cis-1-(4-chlorophenyl)-2-(1H-1,2,4-triazole-1-yl)-cycloheptanol, methyl 1-(2,3-dihydro-2,2-dimethyl-1H-inden-1-yl)-1H-imidazole-5-carboxylate, 3,4,5-trichloro-2,6-pyridinedicarbonitrile, Methyl 2-[[[cyclopropyl[(4-methoxyphenyl)imino]methyl]thio]methyl]-.alpha.-(methoxymethylene)-benzeneacetate, 4-chloro-alpha-propynyloxy-N-[2-[3-methoxy-4-(2-propynyloxy)phenyl]ethyl]-benzeneacetamide, (2S)-N-[2-[4-[(3-(4-chlorophenyl)-2-propynyl]oxy]-3-methoxyphenyl]ethyl]-3-methyl-2-[(methylsulfonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propyl-benzopyranon-4-one, N-{(Z)-[(cyclopropylmethoxy)imino][6-(difluoromethoxy)-2,3-difluorophenyl]methyl}-2-phenylacetamide, N-(3-ethyl-3,5,5-trimethyl-cyclohexyl)-3-formylamino-2-hydroxy-benzamide, 2-[[[[1-[3(1 Fluoro-2-phenylethyl)oxy]phenyl]ethylidene]amino]oxy]methyl]-alpha-(methoxyimino)-N-methyl-alphaE-benzeneacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, 2-(2-{[6-(3-chloro-2- methylphenoxy)-5-fluoropyrimidin-4-yl]oxy}phenyl)-2-(methoxyimino)-N-methylacetamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid.

The composition according to the invention comprising a mixture of a compound of formula (I) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compound of formula (I) and the fungicide composition according to the invention can be used to curatively or preventively control the phytopathogenic fungi of plants or crops. Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

In the same manner, the compound of formula (I) and the insecticide composition according to the invention can be used to curatively or preventively control damaging insects, notably of plants or crops. Thus, according to a further aspect of the invention, there is provided a method for curatively or preventively controlling damaging insects, notably of plants or crops, characterised in that a compound of formula (I) or an insecticide composition according to the invention is applied to the seed, the plant or to the fruit of the plant or to the soil wherein the plant is growing or wherein it is desired to grow.

The method of treatment according to the invention may also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

Among the plants that can be protected by the method according to the invention, mention may be made of: cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubieceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferee* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots) horticultural and forest crops; as well as genetically modified homologues of these crops.

Among the diseases of plants or crops that can be controlled by the method according to the invention, mention may be made of:

Powdery mildew diseases such as:
*Blumeria* diseases, caused for example by *Blumeria graminis*;
*Podosphaera* diseases, caused for example by *Podosphaera leucotricha*;
*Sphaerotheca* diseases, caused for example by *Sphaerotheca fuliginea*;
*Uncinula* diseases, caused for example by *Uncinula necator*;
Rust diseases such as:
*Gymnosporangium* diseases, caused for example by *Gymnosporangium sabinae*;
*Hemileia* diseases, caused for example by *Hemileia vastatrix*;
*Phakopsora* diseases, caused for example by *Phakopsora pachyrhizi* or *Phakopsora meibomiae*;
*Puccinia* diseases, caused for example by *Puccinia recondite*;
*Uromyces* diseases, caused for example by *Uromyces appendiculatus*;
Oomycete diseases such as:
*Bremia* diseases, caused for example by *Bremia lactucae*;
*Peronospora* diseases, caused for example by *Peronospora pisi* or *P. brassicae*;
*Phytophthora* diseases, caused for example by *Phytophthora infestans*;
*Plasmopara* diseases, caused for example by *Plasmopara viticola*;
*Pseudoperonospora* diseases, caused for example by *Pseudoperonospora humuli* or *Pseudoperonospora cubensis*;
*Pythium* diseases, caused for example by *Pythium ultimum*;
Leafspot, leaf blotch and leaf blight diseases such as:
*Alternaria* diseases, caused for example by *Alternaria solani*;
*Cercospora* diseases, caused for example by *Cercospora beticola*;
*Cladiosporum* diseases, caused for example by *Cladiosporium cucumerinum*;
*Cochliobolus* diseases, caused for example by *Cochliobolus sativus*;
*Colletotrichum* diseases, caused for example by *Colletotdichum lindemuthanium*;
*Cycloconium* diseases, caused for example by *Cycloconium oleaginum*;
*Diaporthe* diseases, caused for example by *Diaporthe citri*;
*Elsinoe* diseases, caused for example by *Elsinoe fawettii*;
*Gloeosporium* diseases, caused for example by *Gloeosporium laeticolor*;
*Glomerella* diseases, caused for example by *Glomerella cingulata*;
*Guignardia* diseases, caused for example by *Guignardia bidwelli*;
*Leptosphaeria* diseases, caused for example by *Leptosphaeria maculans*; *Leptosphaeria nodorum*;
*Magnaporthe* diseases, caused for example by *Magnaporthe grisea*;
*Mycosphaerella* diseases, caused for example by *Mycosphaerella graminicola Mycosphaerella arachidicola*; *Mycosphaerella fijiensis*;
*Phaeosphaeria* diseases, caused for example by *Phaeosphaeria nodorum*;
*Pyrenophora* diseases, caused for example by *Pyrenophora teres*;

*Ramularia* diseases, caused for example by *Ramularia collo-cygni*;
*Rhynchosporium* diseases, caused for example by *Rhynchosporium secalis*;
*Septoria* diseases, caused for example by *Septoria apii* or *Septoria lycopercisi*;
*Typhula* diseases, caused for example by *Typhula incarnata*;
*Venturia* diseases, caused for example by *Venturia inaequalis*;
Root and stem diseases such as:
*Corticium* diseases, caused for example by *Corticium graminearum*;
*Fusarium* diseases, caused for example by *Fusarium oxysporum*;
*Gaeumannomyces* diseases, caused for example by *Gaeumannomyces graminis*;
*Rhizoctonia* diseases, caused for example by *Rhizoctonia solani*;
*Tapesia* diseases, caused for example by *Tapesia acuformis*;
*Thielaviopsis* diseases, caused for example by *Thielaviopsis basicola*;
Ear and panicle diseases such as:
*Alternaria* diseases, caused for example by *Alternaria* spp.
*Aspergillus* diseases, caused for example by *Aspergillus flavus*;
*Cladosporium* diseases, caused for example by *Cladosporium* spp.
*Claviceps* diseases, caused for example by *Claviceps purpurea*;
*Fusarium* diseases, caused for example by *Fusarium culmorum*;
*Gibberella* diseases, caused for example by *Gibberella zeae*;
*Monographella* diseases, caused for example by *Monographella nivalis*;
Smut and bunt diseases such as:
*Sphacelotheca* diseases, caused for example by *Sphacelotheca reiliana*;
*Tilletia* diseases, caused for example by *Tilletia caries*;
*Urocystis* diseases, caused for example by *Urocystis occulta*;
*Ustilago* diseases, caused for example by *Ustilago nuda*;
Fruit rot and mould diseases such as:
*Aspergillus* diseases, caused for example by *Aspergillus flavus*:
*Botrytis* diseases, caused for example by *Botrytis cinerea*;
*Penicillium* diseases, caused for example by *Penicillium expansum*;
*Sclerotinia* diseases, caused for example by *Sclerotinia sclerotiorum*;
*Verticilium* diseases, caused for example by *Verticilium alboatrum*;
Seed and soilborne decay, mould, wilt, rot and damping-off diseases:
*Fusarium* diseases, caused for example by *Fusarium culmorum*;
*Phytophthora* diseases, caused for example by *Phytophthora cactorum*;
*Pythium* diseases, caused for example by *Pythium ultimum*;
*Rhizoctonia* diseases, caused for example by *Rhizoctonia solani*;
*Sclerotium* diseases, caused for example by *Sclerotium rolfsii*;
*Microdochium* diseases, caused for example by *Microdochium nivale*;
Canker, broom and dieback diseases such as:
*Nectria* diseases, caused for example by *Nectria galligena*;
Blight diseases such as:
*Monilinia* diseases, caused for example by *Monilinia laxa*;
Leaf blister or leaf curl diseases such as:
*Taphrina* diseases, caused for example by *Taphrina deformans*;
Decline diseases of wooden plants such as:
Esca diseases, caused for example by *Phaemoniella clamydospora*;
*Eutypa* dyeback, caused for example by *Eutypa lata*;
Dutch elm disease, caused for example by *Ceratocystsc ulmi*;
Diseases of flowers and Seeds such as:
*Botrytis* diseases, caused for example by *Botrytis cinerea*;
Diseases of tubers such as:
*Rhizoctonia* diseases, caused for example by *Rhizoctonia solani*.

Among the damaging pests or insects that can be controlled at any development stage according to the insecticide method of the invention, mention may be made to:
the order of the *Anoplura* (*Phthiraptera*), for example, *Damalinia* spp., *Haematopinus* spp., *Linognathus* spp., *Pediculus* spp., *Trichodectes* spp.;
the class of the *Arachnida*, for example, *Acarus siro*, *Aceria sheldoni*, *Aculops* spp., *Aculus* spp., *Amblyomma* spp., *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., Hemifarsonemus spp., *Hyalomma* spp., *Ixodes* spp., *Latrodectus mactans*, *Metatetranychus* spp., *Oligonychus* spp., *Ornitho-doros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*;
the class of the *Bivalva*, for example, *Dreissena* spp.;
the order of the *Chilopoda*, for example, *Geophilus* spp., *Scutigera* spp.;
the order of the *Coleoptera*, for example, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apogonia* spp., *Atomaria* spp., *Attagenus* spp., *Bruchidius obtectus*, *Bruchus* spp., *Ceuthorhynchus* spp., *Cleonus mendicus*, *Conoderus* spp., *Cosmopolites* spp., *Costelytra zealandica*, *Curculio* spp., *Cryptorhynchus lapathi*, *Dermestes* spp., *Diabrotica* spp., *Epilachna* spp., *Faustinus cubae*, *Gibbium psylloides*, *Heteronychus arator*, *Hylamorpha elegans*, *Hylotrupes bajulus*, *Hypera postica*, *Hypothenemus* spp., *Lachnostema consanguinea*, *Leptinotarsa decemlineata*, *Lissorhopfrus oryzophilus*, *Lixus* spp., *Lyctus* spp., *Meligethes aeneus*, *Melolontha melolontha*, *Migdolus* spp., *Monochamus* spp., *Naupactus xanthographus*, *Niptus hololeucus*, *Oryctes rhinoceros*, *Oryzaephilus surinamensis*, *Otiorrhynchus sulcatus*, *Oxycetonia jucunda*, *Phaedon cochleariae*, *Phyllophaga* spp., *Popillia japonica*, *Premnotrypes* spp., *Psylliodes chrysocephala*, *Ptinus* spp., *Rhizobius ventralis*, *Rhizopertha dominica*, *Sitophilus* spp., *Sphenophorus* spp., *Stemechus* spp., *Symphyletes* spp., *Tenebrio molitor*, *Tribolium* spp., *Trogoderma* spp., *Tychius* spp., *Xylotrechus* spp., *Zabrus* spp.

the order of the *Collembola*, for example, *Onychiurus armatus;* the order of the *Dermaptera*, for example, *Forficula auricularia;* the order of the *Diplopoda*, for example, *Blaniulus guttulatus;* the order of the *Diptera*, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohifahrtia* spp;

the class of the *Gastropoda*, for example, *Arion* spp., *Biomphalaria* spp., *Bulinus* spp., *Deroceras* spp., *Galba* spp., *Lymnaea* spp., *Oncomelania* spp., *Succinea* spp.;

the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti;*

Protozoa, such as *Eimeria;* the order of the *Heteroptera*, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris heweffi, Dysdercus* spp., *Euschistus* spp., *Euryguster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp;

the order of the *Homoptera*, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calli-gypona marginata, Cameocephala fulgida, Ceratovacuna lanigera, Cercopidae, Cero-plastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;* the order of the *Hymenoptera*, for example, *Diprion* spp., *Hoplocampa* spp., *Lasius* spp., *Monomorium pharaonis, Vespa* spp.;

the order of the *Isopoda*, for example, *Armadillidium vulgare, Oniscus asellus, Porcellio scaber;* the order of the *Isoptera*, for example, *Reticulitermes* spp., *Odontotermes* spp.;

the order of the *Lepidoptera*, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Toftrix viridana, Trichoplusia* spp.;

the order of the *Orthoptera*, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria;* the order of the *Siphonaptera*, for example, *Ceratophyllus* spp., *Xenopsylla cheopis.* the order of the *Symphyla*, for example, *Scutigerella immaculate;* the order of the *Thysanoptera*, for example, *Baliothrips biformis, Enneothrips flavens, Frankliniella* spp., *Heliothrips* spp., *Hercinothrips femoralls, Kakothrips* spp., *Rhipiphorothrips cruentatus, Scirtothrips* spp., *Taeniothrips cardamoni, Thrips* spp.;

the order of the *Thysanura*, for example, *Lepisma saccharina;* the phytoparasitic nematodes including for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp;

the beetles, such as *Hylotrupes bajulus*, *Chlorophorus pilosis*, *Anobium punctatum*, *Xestobium rufovillosum*, *Ptilinus pecticornis*, *Dendrobium pertinex*, *Emobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec. *Tryptodendron* spec. *Apate monachus*, *Bostrychus capucins*, *Heterobostrychus brunneus*, *Sinoxylon* spec. *Dinoderus minutus;*

Hymenopterons, such as *Sirex juvencus*, *Urocerus gigas*, *Urocerus gigas taignus*, *Urocerus augur;* termites, such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis*, *Coptotermes formosanus;*

Bristletails, such as *Lepisma saccharina;* the order of the *Acarina*, for example, *Argas persicus*, *Argas reflexus*, *Bryobia* ssp., *Dermanyssus gallinae*, *Glyciphagus domesticus*, *Ornithodorus moubat*, *Rhipicephalus sanguineus*, *Trombicula alfreddugesi*, *Neutrombicula autumnalis*, *Dermatophagoides pteronissimus*, *Dermatophagoides forinae;* the order of the *Araneae*, for example, *Avicularriidae*, *Araneidae;* the order of the *Opiliones*, for example, *Pseudoscorpiones chelifer*, *Pseudoscorpiones cheiridium*, *Opiliones phalangium;* the order of the *Isopoda*, for example, *Oniscus asellus*, *Porcellio scaber;* the order of the *Diplopoda*, for example, *Blaniulus guttulatus*, *Polydesmus* spp.;

the order of the *Chilopoda*, for example, *Geophilus* spp.;

the order of the *Zygentoma*, for example, *Ctenolepisma* spp., *Lepisma saccharina*, *Lepismodes inquilinus;* the order of the *Blattaria*, for example, *Blatta orientalies*, *Blattella germanica*, *Blattella asahinai*, *Leucophaea maderae*, *Panchlora* spp., *Parcoblatta* spp., *Periplaneta australasiae*, *Periplaneta americana*, *Periplaneta brunnea*, *Periplaneta fuliginosa*, *Supella longipalpa;* the order of the *Saltatoria*, for example, *Acheta domesticus;* the order of the *Dermaptera*, for example, *Forficula auricularia;* the order of the *Isoptera*, for example, *Kaloternes* spp., *Reticulitermes* spp;

the order of the *Psocoptera*, for example, *Lepinatus* spp., *Liposcelis* spp;

the order of the *Coleoptera*, for example, *Anthrenus* spp., *Attagenus* spp., *Dermestes* spp.; *Latheticus oryzae*, *Necrobia* spp., *Ptinus* spp., *Rhizopertha dominica*, *Sitophilus granarius*, *Sitophilus oryzae*, *Sitophilus zeamais*, *Stegobium paniceum.* the order of the *Diptera*, for example, *Aedes aegypti*, *Aedes albopictus*, *Aedes taeniorhynchus*, *Anopheles* spp., *Calliphora erythrocephala*, *Chrysozona pluvialis*, *Culex quinquefasciatus*, *Culex pipiens*, *Culex tarsalis*, *Drosophila* spp., *Fannia canicularis*, *Musca domestica*, *Phlebotomus* spp., *Sarcophaga camaria*, *Simulium* spp., *Stomoxys calcitrans*, *Tipula paludosa;* the order of the *Lepidoptera*, for example, *Achroia grisella*, *Galleria mellonella*, *Plodia interpunctella*, *Tinea cloacella*, *Tinea pellionella*, *Tineola bisselliella;* the order of the *Siphonaptera*, for example, *Ctenocephalides canis*, *Ctenocephalides felis*, *Pulex irritans*, *Tunga penetrans*, *Xenopsylla cheopis.* the order of the *Hymenoptera*, for example, *Camponotus herculeanus*, *Lasius fuliginosus*, *Lasius niger*, *Lasius umbratus*, *Monomorium pharaonis*, *Paravespula* spp., *Tetramorium caespitum;* the order of the *Anoplura*, for example, *Pediculus humanus capitis*, *Pediculus humanus corporis*, *Pemphigus* spp., *Phylloera vastatrix*, *Phthirus pubis;* the order of the *Heteroptera*, for example, *Cimex hemipterus*, *Cimex lectularius*, *Rhodinus prolixus*, *Triatoma infestans.*

The fungicide or insecticide composition according to the invention may also be used against fungal diseases or damaging insects liable to grow or attack on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The fungicide or insecticide composition according to the invention may also be used in the treatment of genetically modified organisms with the compounds according to the invention or the agrochemical compositions according to the invention. Genetically modified plants are plants into genome of which a heterologous gene encoding a protein of interest has been stably integrated. The expression "heterologous gene encoding a protein of interest" essentially means genes which give the transformed plant new agronomic properties, or genes for improving the agronomic quality of the modified plant.

The compounds or mixtures according to the invention may also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus.*

The various aspects of the invention will now be illustrated with reference to the following tables of compounds and examples. The following tables illustrate in a non-limiting manner examples of compounds according to the invention.

In the following examples, M+1 (or M−1) means the molecular ion peak, plus or minus 1 a.m.u. (atomic mass unit) respectively, as observed in mass spectroscopy and M (Apcl+) means the molecular ion peak as it was found via positive atmospheric pressure chemical ionisation in mass spectroscopy.

In the following examples, the logP values were determined in accordance with EEC Directive 79/831 Annex V.A8 by HPLC (High Performance Liquid Chromatography) on a reversed-phase column (C18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known logP values (determination of the logP values by the retention times using linear interpolation between two successive alkanones).

The lambda max values were determined in the maxima of the chromatographic signals using the UV spectra from 190 nm to 400 nm.

PREPARATION EXAMPLE 1

N-ethyl-N-methyl-N'-[4-(naphthyl-2-oxy)-2,5-xylyl]form-amidine—process (d)—compound (VIII) to compound (I)

0.25 g (0.97 mmol) of 4-(naphthyl-2-oxy)-2,5-xylidine were dissolved in 5 ml of methanol and treated with 0.23 g (1.35 mmol) of a solution of N-ethyl-N-methylformamid-dimethylacetal in methanol (77%). The reaction mixture was stirred at 45° C. for 8 h before the solvent was removed in vacuo to yield after column chromatography on silica gel (cyclohexane/ethyl acetate) 220 mg (67% yield, 98% purity) of product; log P (pH 2.3)=2.38.
Preparation of Starting Material:

4-(naphthyl-2-oxy)-2,5-xylidine—process (b)—compound (V) to compound (VIII)

3.2 g (10.9 mmol) of 4-(naphthyl-2-oxy)-2,5-dimethylnitrobenzene were dissolved in 20 ml of methanol and 20 ml of concentrated hydrochloric acid before 7.39 g (32.7 mmol) of stannous chloride were added. The reaction mixture was refluxed for 6 h, cooled to room temperature and extracted with dichloromethane (2×50 ml). The combined organic layers were washed with 1-N sodium hydroxide solution, then dried ($MgSO_4$), filtered and evaporated to dryness to yield 2.85 g of product (89% yield, 90% purity); log P (pH 2.3)=2.80.

4-(naphthyl-2-oxy)-2,5-dimethylnitrobenzene—Process (a)—compound (III and IV) to compound (V)

3.00 g (16.16 mmol) of 4-chloro-2,5-dimethylnitrobenzene, 2.56 g (17.78 mmol) of 2-hydroxy-naphthaline and 3.13 g (22.63 mmol) of potassium carbonate were suspended in 25 ml of dimethylformamide. The reaction mixture was refluxed for 12 h, cooled down to room temperature, treated with 100 ml of water and 50 ml of a 1N solution of sodium hydroxide in water and extracted with dichloromethane (2×100 ml). The combined organic extracts were washed with 1N solution of hydrochloric acid, dried ($MgSO_4$), filtered and evaporated to dryness. The crude product was purified by silica gel chromatography eluting with cyclohexane/ethyl acetate to yield the title compound in 65% yield (3.49 g, 88% purity); log P (pH 2.3)=5.04.

PREPARATION EXAMPLE 2

Piperidinyl-N-[4-(naphthyl-2-oxy)-2,5-xylyl]form-amidine—process (d)—compound (VIII) to compound (I)

0.50 g (1.90 mmol) of 4-(naphthyl-2-oxy)-2,5-xylidine and 5 mg of p-toluene sulfonic acid were refluxed in 5 ml of trimethylformiate for 3 h. The reaction mixture was cooled to room temperature and the solvent was removed in vacuo. The residue was dissolved in 50 ml of dichloromethane and subsequently treated with 0.24 g (2.85 mmol) of piperidine and stirred at room temperature for 16 h. The crude product was purified by silica gel chromatography eluting with methanol/dichloromethane to yield the title compound in 47% yield (0.36 g, 90% purity); log P (pH 2.3)=2.51.
Preparation of Starting Material:

4-(naphthyl-2-oxy)-2,5-xvlidine—Process (b)—compound (V) to compound (VIII)

13.0 g (44 mmol) of 4-(naphthyl-2-oxy)-2,5-dimethylnitrobenzene were dissolved in 250 ml of methanol and 1.7 g Palladium (10% on charcoal) and 12.57 g (199 mmol) of ammonium formiate were added. The reaction mixture was stirred at room temperature for 18 h, further 2 h at 50° C., cooled to room temperature and extracted with dichloromethane (2×50 ml). The combined organic layers were dried ($MgSO_4$), filtered and evaporated to dryness to yield 11.9 g of crude product (yield 66%, purity 65%); log P (pH 2.3)=2.75.

PREPARATION EXAMPLE 3

N-ethyl-N-methyl-N'-[4-(naphthyl-2-oxy)-2,5-xylyl]form-amidine hydrochloric acid salt—process (e)—compound (I) to Compound (Ia)

1.40 g (0.42 mmol) of N-ethyl-N-methyl-N'-[4-(naphthyl-2-oxy)-2,5-xylyl]form-amidine were dissolved in 10 ml of dioxane and treated with 2 ml of a 4 molar solution of hydrochloric acid in dioxane. The reaction mixture was stirred at room temperature for 2 h before the solvent was removed in vacuo. The residue was stirred with t-Butylmethylether and the resulting white grey crystals were dried to yield 110 mg (68% yield, 96% purity) of product; mp=203.4° C.

TABLE 1

(I)

| N° | $R^1$ | $R^2$ | $R^3$ | $R^4$ | $R^5$ | $R^6$ | $logP_a$ |
|---|---|---|---|---|---|---|---|
| 4 | H | Me | iPr | Me | Me | H | 2.52 |
| 5 | H | Me | Et | Me | Me | 7-OH | 1.92 |
| 6 | H | Me | iPr | Me | Me | 7-OH | 2.02 |
| 7 | H | Me | iPr | Me | Me | 6-Br | 2.92 |

TABLE 1-continued (I)

| N° | R¹ | R² | R³ | R⁴ | R⁵ | R⁶ | logP$_a$ |
|---|---|---|---|---|---|---|---|
| 8 | H | Me | Et | Me | Me | 6-Br | 2.69 |
| 9 | H | Me | nPr | Me | Me | 6-Br | 2.89 |
| 10 | H | Me | nPr | Me | Me | 6-CN | 2.23 |
| 11 | H | Me | Et | Me | Me | 6-CN | 2.07 |
| 12 | H | Me | iPr | Me | Me | 6-CN | 2.20 |
| 13 | H | Me | iPr | Me | Me | 6-CO—C$_6$H$_5$ | 2.75 |
| 14 | H | Me | Et | Me | Me | 6-CO—C$_6$H$_5$ | 2.66 |
| 15 | H | Me | nPr | Me | Me | 6-CO—C$_6$H$_5$ | 2.77 |
| 16 | H | Me | iPr | Me | Me | 7-OMe | 2.56 |
| 17 | H | Me | Et | Me | Me | 7-OMe | 2.44 |
| 18 | H | Me | nPr | Me | Me | 7-OMe | 2.61 |
| 19 | H | Me | Et | Me | Me | 6-CH(OH)—C$_6$H$_5$ | 2.21 |
| 20 | H | Me | iPr | Me | Me | 7-NH—(CH$_2$)$_3$-Me | 2.91 |
| 21 | H | —(CH$_2$)$_2$—O—(CH$_2$)$_2$— | | Me | Me | H | 2.21 |
| 22 | H | —(CH$_2$)$_2$—NH—(CH$_2$)$_2$— | | Me | Me | H | 1.55 |
| 23 | H | —(CH$_2$)$_2$—N(CH$_3$)—(CH$_2$)$_2$— | | Me | Me | H | 1.64 |
| 24 | H | Me | Et | Me | Me | 7-NH—(CH$_2$)$_3$-Me | 2.62 |
| 25 | H | Me | nPr | Me | Me | 7-NH—(CH$_2$)$_3$-Me | 2.91 |
| 26 | H | —(CH$_2$)$_4$— | | Me | Me | H | 2.33 |
| 27 | H | Me | iPr | Me | Me | 6-CH(=N-OMe)-C$_6$H$_5$ | 3.20 |
| 28 | H | Me | Et | Me | Me | 6-CH(=N-OMe)-C$_6$H$_5$ | 3.05 |
| 29 | H | Me | nPr | Me | Me | 6-CH(=N-OMe)-C$_6$H$_5$ | 3.14 |
| 30 | H | Me | iPr | Me | Me | 6-OMe | 2.70 |
| 31 | H | Me | iPr | Me | Me | 6-[(2-OH-Et)NSO$_2$] | 1.75 |

TABLE 2

(I)

| N° | R¹ | R² | R³ | R⁴ | R⁵ | R⁶ | logP$_a$ |
|---|---|---|---|---|---|---|---|
| 32 | H | Me | Et | Me | Me | H | 2.43 |
| 33 | H | Me | Et | Me | Me | H | 2.57 |

TABLE 3

(Ia)

| N° | R¹ | R² | R³ | R⁴ | R⁵ | R⁶ | R | logP$_a$ |
|---|---|---|---|---|---|---|---|---|
| 34 | H | Me | Et | Me | Me | H | CH$_3$COO | 2.33 |
| 35 | H | Me | Et | Me | Me | H | HOOC—COO | 2.25 |
| 36 | H | Me | Et | Me | Me | H | C$_6$H$_5$COO | 2.44 |

EFFICACY EXAMPLE A

Efficacy Example A: in vivo Preventive Test on *Puccinia recondita* f. Sp. *tritici* (Wheat Brown Rust)

| Solvent: | 50 parts by weight of n,n-dimethylacetamid |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are inoculated with a spore suspension of *Puccinia recondita* in a 0.1% strength aqueous agar solution. After the spray coating has dried on, the plants are sprayed with the preparation of active compound at the stated rate of application. The plants remain for 24 hours in an incubation cabinet at 20° C. and a relative atmospheric humidity of 100%.

The plants are placed in a greenhouse at a temperature of approximately 20° C. and a relative atmospheric humidity of approximately 80% to promote the development of rust pustules.

The test is evaluated 10 days after the inoculation. 0% means an efficacy which corresponds to that of the control, while an efficacy of 100% means that no disease is observed. In this test the following compounds according to the invention showed an efficacy of 70% or even higher at a concentration of 1000 ppm of active ingredient: 1, 4, 32, 33.

EFFICACY EXAMPLE B

Efficacy Example B: in vivo Preventive Test on *Erysiphe gramini* (Powdery Mildew on Barley)

| Solvent: | 50 parts by weight of n,n-dimethylacetamid |
| --- | --- |
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has dried on, the plants are dusted with spores of *Erysiphe graminis* f.sp. *hordei*.

The plants are placed in a greenhouse at a temperature of approximately 20° C. and a relative atmospheric humidity of approximately 80% to promote the development of mildew pustules.

The test is evaluated 7 days after the inoculation. 0% means an efficacy which corresponds to that of the control, while an efficacy of 100% means that no disease is observed.

In this test the following compounds according to the invention showed an efficacy of 70% or even higher at a concentration of 1000 ppm of active ingredient: 1, 4, 32, 33.

EFFICACY EXAMPLE C

Efficacy Example C: in vivo Protective Test on *Alternaria solani* (Leaf Spot of Tomato)

| Solvent: | 49 parts by weight of N, N-dimethylformamide |
| --- | --- |
| Emulsifier: | 1 part by weight of alkylarylpolyglycolether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of *Alternaria solani*. The plants remain for one day in an incubation cabinet at approximately 20° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the control while an efficacy of 100% means that no disease is observed. In this test, invention related compounds of the following formula revealed an efficacy of 70% or higher at a concentration of 500 ppm of active ingredient: 1, 20, 28, 32, 35.

EFFICACY EXAMPLE D in vivo Protective Test on *Podosphaera leucotricha* (Apples)

| Solvent: | 24.5 parts by weight of acetone |
| --- | --- |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of the causal agent of apple mildew (*Podosphaera leucotricha*). The plants are then placed in a greenhouse at approximately 23° C. and a relative atmospheric humidity of approximately 70%.

The test is evaluated 10 days after the inoculation. 0% means an efficacy which corresponds to that of the control, while an efficacy of 100% means that no disease is observed. In this test the compounds according to the invention of the following structures showed efficacy of 70% or even higher at a concentration of 100 ppm of active ingredient: 1, 4, 32, 33.

EFFICACY EXAMPLE E

Efficacy Example E: in vivo Protective Test on *Botrytis cinerea* (Cucumbers)

| Solvent: | 49 parts by weight of N, N-dimethylformamide |
| --- | --- |
| Emulsifier: | 1 part by weight of alkylarylpolyglycolether |

To produce a suitable preparation of active compound, 1 part by weight of active compound is mixed with the stated amounts of solvent and emulsifier, and the concentrate is diluted with water to the desired concentration.

To test for protective activity, young cucumber plants are sprayed with the preparation of active compound at the stated rate of application. One day after this treatment, plants are inoculated with a spore suspension of *Botrytis cinerea*. The plants remain then for one day in an incubation cabinet at approximately 20° C. and a relative atmospheric humidity of 100%. Then, the plants are placed in an incubation cabinet at approximately 13° C. and a relative atmospheric humidity of 96%.

The test is evaluated 5-6 days after the inoculation. 0% means an efficacy which corresponds to that of the control while an efficacy of 100% means that no disease is observed.

In this test, invention related compounds of the following formula revealed an efficacy of 70% or higher at a concentration of 500 ppm of active ingredient: 2, 3, 4, 5, 6, 7, 8, 13, 14, 19, 22, 23, 24, 27, 28, 29, 32, 33.

EFFICACY EXAMPLE F in vivo Protective Test on *Uromyces appendiculatus* (Beans)

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of the causal agent of bean rust (*Uromyces appendiculatus*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the control, while an efficacy of 100% means that no disease is observed.

In this test the compounds according to the invention of the following structures showed efficacy of 70% or even higher at a concentration of 100 ppm of active ingredient: 8, 10, 11, 12, 13, 16, 17, 18, 19.

EFFICACY EXAMPLE G in vivo Protective Test on *Venturia inequaelis* (Apples)

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the control, while an efficacy of 100% means that no disease is observed.

In this test the compounds according to the invention of the following structures showed efficacy of 70% or even higher at a concentration of 100 ppm of active ingredient: 1, 4, 8, 10, 11, 12, 13, 16, 17, 18, 19, 32, 33.

EFFICACY EXAMPLE H in vivo Protective Test on *Myzus persicae* (MYZUPE)

| Solvent: | 78 parts by weight acetone |
| | 1.5 parts by weight dimethylformamide |
| Wetting agent: | 0.5 parts by weight alkylarylpolyglcolether |

To produce a suitable preparation of active compound, 1 part by weight of active compound is mixed with the stated amount of solvent and emulsifier, and the concentrate is diluted with emulsifier-containing water to the desired concentration.

Chinese cabbage (*Brassica pekinesis*) leaf-disks infected with all instars of the green peach aphid (*Myzus persicae*), are sprayed with a preparation of the active ingredient at the desired concentration.

After the specified period of time, mortality in % is determined. 100% means that all aphids have been killed; 0% means that none of the aphids have been killed.

In this test for example, the following compounds from the preparation examples showed good activity: 17.

EFFICACY EXAMPLE I in vivo Protective Test on *Heliothis viresens* (HELIVI)

| Solvent: | 78 parts by weight acetone |
| | 1.5 parts by weight dimethylformamide |
| Wetting agent: | 0.5 parts by weight alkylarylpolyglcolether |

To produce a suitable preparation of active compound, 1 part by weight of active compound is mixed with the stated amount of solvent and emulsifier, and the concentrate is diluted with emulsifier-containing water to the desired concentration.

Soybean (*Glycine max.*) leaf sections are sprayed with a preparation of the active ingredient of the desired concentration. Once dry, the leaf sections are infested with eggs of cotton bollworm (*Heliotis virescens*).

After the specified period of time, mortality in % is determined. 100% means that all eggs have been killed and 0% means that none of the eggs have been killed.

In this test for example, the following compounds from the preparation examples showed good activity: 10, 13.

The invention claimed is:

1. A phenyl-amidine derivative of formula (I):

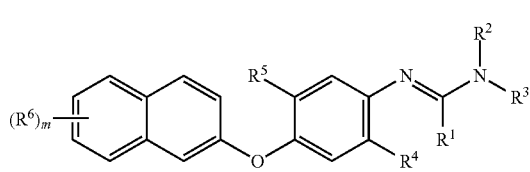

wherein
R$^1$ represents H;
R$^2$ represents a substituted or non substituted C$_1$-C$_{12}$-alkyl;
R$^3$ represents a substituted or non substituted C$_2$-C$_{12}$-alkyl, substituted or non substituted C$_3$-C$_6$-cycloalkyl, substituted or non substituted C$_2$-C$_{12}$-alkenyl, substituted or non substituted C$_2$-C$_{12}$-alkynyl, halogeno-C$_1$-C$_{12}$-alkyl; or
R$^1$ and R$^2$, R$^1$ and R$^3$ or R$^2$ and R$^3$ can form together a substituted or non substituted 5 to 7-membered heterocycle;
R$^4$ represents a substituted or non substituted C$_1$-C$_{12}$-alkyl, a halogen atom, halogeno-C$_1$-C$_{12}$-alkyl, substituted or non substituted O—C$_1$-C$_{12}$-alkyl or cyano;
R$^5$ represents H, a substituted or non substituted C$_1$-C$_{12}$-alkyl, a halogen atom, halogeno-C$_1$-C$_{12}$-alkyl, substituted or non substituted O—C$_1$-C$_{12}$-alkyl or cyano;
R$^6$ represents H, halogen, CN, substituted or non substituted phenoxy, substituted or non substituted C$_1$-C$_{12}$-alkyl, halogeno-C$_1$-C$_{12}$-alkyl, OR$^7$, SR$^7$, trialkyl-silyl, COR$^7$, COOR$^7$, C(R$^7$)=NOR$^7$; NR$^7$R$^8$, CONR$^7$R$^8$, SO$_2$NR$^7$R$^8$, SONR$^7$R$^8$;
R$^7$, R$^8$ represent independently H, substituted or non substituted C$_1$-C$_{12}$-alkyl, aryl or R$^7$ and R$^8$ can form a substituted or non substituted, saturated or non saturated 5 to 7-membered heterocycle including one or more atoms selected in the list consisting of O, N and S;
m represents 1, 2, 3 or 4;
as well as a salt; N-oxide; metallic complex, metalloidic complex and/or optically active isomer thereof.

2. A compound of formula (I) according to claim 1 wherein
R$^1$ represents H;
R$^2$ represents methyl; or
R$^3$ represents C$_2$-C$_{12}$-alkyl, C$_2$-C$_{12}$-alkenyl or C$_3$-C$_6$-cycloalkyl; or
R$^2$ and R$^3$ can form together a substituted or non substituted 5 to 7-membered heterocycle; or
R$^4$ represents C$_1$-C$_{12}$-alkyl or a halogen atom; or
R$^5$ represents a C$_1$-C$_{12}$-alkyl or a halogen atom; or
R$^6$ represents substituted C$_1$-C$_{12}$-alkyl.

3. A compound of formula (I) according to claim 1 wherein
R$^1$ represents H;
R$^3$ represents a non substituted C$_2$-C$_4$-alkyl or C$_3$-C$_4$-alkenyl; or
R$^2$ and R$^3$ can form together a 6-membered heterocycle; or
R$^4$ represents a non substituted C$_1$-C$_{12}$-alkyl or a chlorine atom; or
R$^5$ represents a non substituted C$_1$-C$_{12}$-alkyl or a chlorine atom; or
R$^6$ represents a branched C$_1$-C$_{12}$-alkyl.

4. A compound of formula (I) according to claim 1 wherein
R$^1$ represents H;
R$^3$ represents ethyl, n-propyl, i-propyl, propenyl, allyl or cyclopropyl; or R$^2$ and R$^3$ can form together a pipiridinyl or a pyrolidinyl; or
R$^4$ represents methyl; or
R$^5$ represents methyl; or
R$^6$ represents CH(OH)R$^7$ or C(R$^7$)=NOR$^8$.

5. A compound of formula (I) according to claim 1 wherein R$^2$ and R$^3$ form together a bis-alkylated-pyrolidinyl.

6. A compound of formula (I) according to claim 5 wherein R$^2$ and R$^3$ form together a bis-methyl-pyrolidinyl.

7. A process for the preparation of a compound of formula (I) according to claim 1, as well as a salt, N-oxide, metallic complex, metalloidic complex and/or optically active isomer thereof, comprising the following steps:

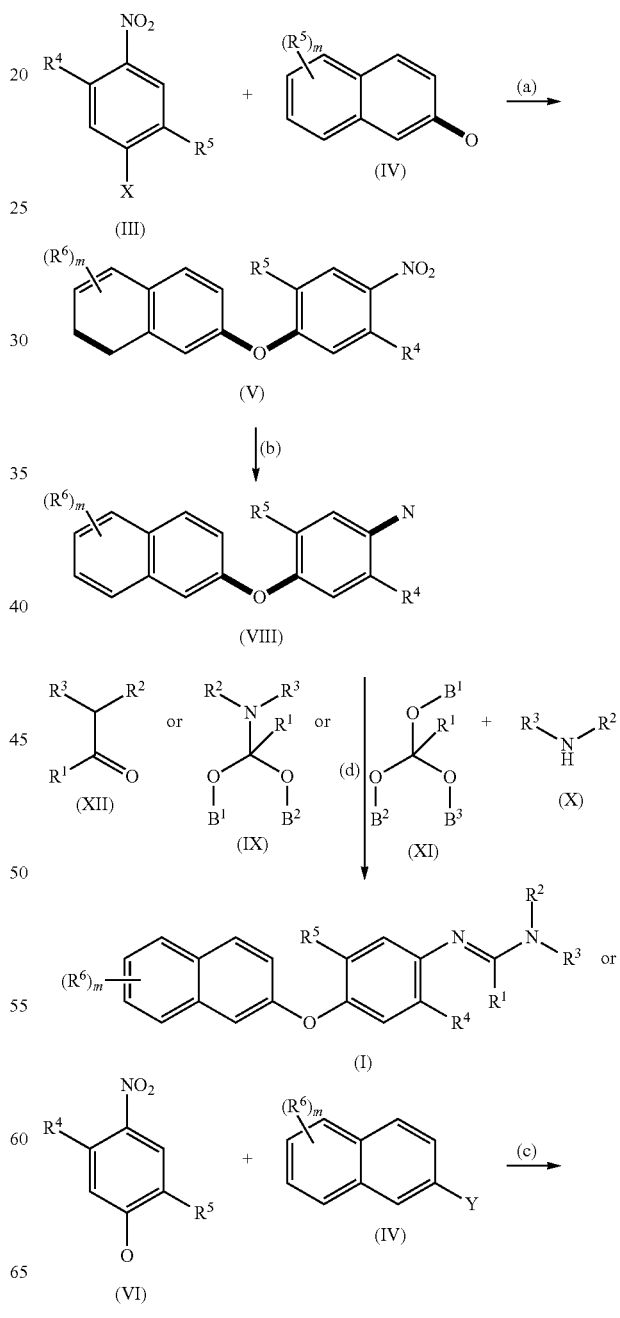

-continued

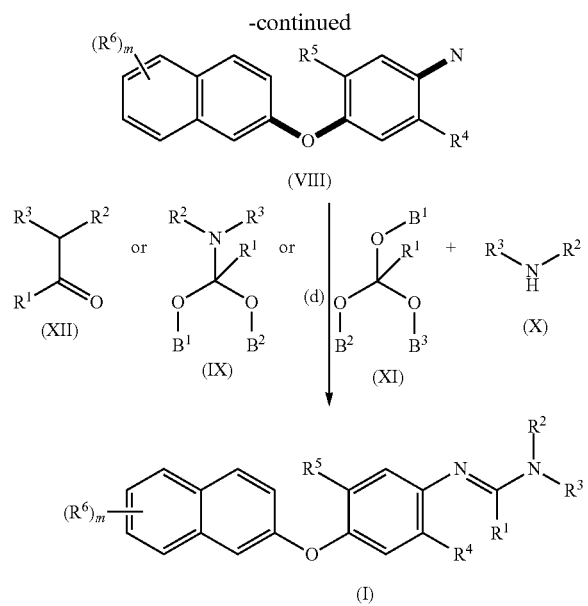

wherein
X represents halogen, triflate, SOMe, mesylate, or tosylate;
Y represents halogen, triflate, SOMe, mesylate, or tosylate;
B1 and B2 represent each alkyl or together cycloalkyl; and
B3 represents alkyl;

And optionally forming a salt, N-oxide, metallic complex, metalloidic complex and/or optically active isomer thereof.

8. A method for controlling phytopathogenic fungi of crops, comprising applying an agronomically effective and substantially non-phytotoxic quantity of a compound according to claim 1 to soil where a plant grows and/or is capable of growing, to leaves and/or fruit of a plant and/or to a seed of a plant.

9. A method for controlling damaging insects comprising applying a compound of formula (I) according to claim 1 to a seed, a plant and/or to fruit of a plant and/or to soil wherein the plant is growing or wherein a plant is desired to grow.

10. A compound of formula (I)

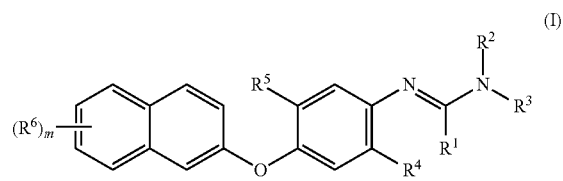

wherein
$R^1$ represents H;
$R^2$ represents methyl;
$R^3$ represents ethyl;
$R^4$ represents methyl;
$R^5$ represents methyl; and
$R^6$ represents H;
m represents 1, 2, 3, or 4;
as well as a salt; N-oxide; metallic complex, metalloidic complex and/or optically active isomer thereof.

11. A phenyl-amidine derivative of formula (I):

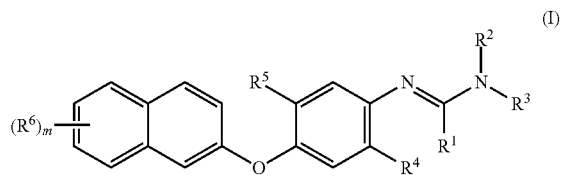

wherein
$R^1$ represents H;
$R^2$ represents a substituted or non substituted $C_1$-$C_{12}$-alkyl;
$R^3$ represents a substituted or non substituted $C_3$-$C_6$-cycloalkyl, a substituted or non substituted $C_2$-$C_{12}$-alkenyl, a substituted or non substituted $C_2$-$C_{12}$-alkynyl, or a halogeno-$C_1$-$C_{12}$-alkyl;
$R^1$ and $R^2$, $R^1$ and $R^3$ or $R^2$ and $R^3$ can form together a substituted or non substituted 5 to 7-membered heterocycle;
$R^4$ represents a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;
$R^5$ represents H, a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;
$R^6$ represents H, halogen, CN, substituted or non substituted phenoxy, substituted or non substituted $C_1$-$C_{12}$-alkyl, halogeno-$C_1$-$C_{12}$-alkyl, $OR^7$, $SR^7$, trialkyl-silyl, $COR^7$, $COOR^7$, $C(R^7)$=$NOR^7$; $NR^7R^8$, $CONR^7R^8$, $SO_2NR^7R^8$, $SONR^7R^8$;
$R^7$, $R^8$ represent independently H, substituted or non substituted $C_1$-$C_{12}$-alkyl, aryl or $R^7$ and $R^8$ can form a substituted or non substituted, saturated or non saturated 5 to 7-membered heterocycle including one or more atoms selected in the list consisting of O, N and S;
m represents 1, 2, 3 or 4;
as well as a salt; N-oxide; metallic complex, metalloidic complex and/or optically active isomer thereof.

12. A compound of formula (I) according to claim 1 wherein $R^3$ represents a non substituted $C_2$-$C_4$-alkyl.

13. A phenyl-amidine derivative of formula (I):

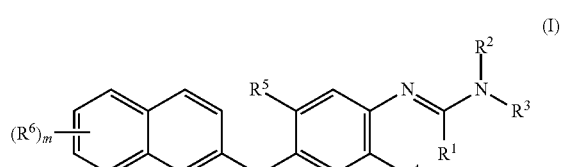

wherein
$R^1$ represents H;
$R^2$ represents a substituted or non substituted $C_1$-$C_{12}$-alkyl;
$R^3$ represents a substituted or non substituted $C_2$-$C_{12}$-alkyl, substituted or non substituted $C_3$-$C_6$-cycloalkyl, substituted or non substituted $C_2$-$C_{12}$-alkenyl, substituted or non substituted $C_2$-$C_{12}$-alkynyl, halogeno-$C_1$-$C_{12}$-alkyl; or
$R^1$ and $R^2$, $R^1$ and $R^3$ or $R^2$ and $R^3$ can form together a substituted or non substituted 5 to 7-membered heterocycle;
$R^4$ represents a halogen atom, a substituted or non substituted $C_1$-$C_{12}$-alkyl, halogeno-$C_1$-$C_{12}$-alkyl, substituted or non substituted O—$C_1$-$C_{12}$-alkyl or cyano;

R⁵ represents H, a substituted or non substituted C₁-C₁₂-alkyl, a halogen atom, halogeno-C₁-C₁₂-alkyl, substituted or non substituted O—C₁-C₁₂-alkyl or cyano;
wherein one of R⁴ or R⁵ represents a halogen atom;
R⁶ represents H, halogen, CN, substituted or non substituted phenoxy, substituted or non substituted C₁-C₁₂-alkyl, halogeno-C₁-C₁₂-alkyl, OR⁷, SR⁷, trialkyl-silyl, COR⁷, COOR⁷, C(R⁷)=NOR⁷; NR⁷R⁸, CONR⁷R⁸, SO₂NR⁷R⁸, SONR⁷R⁸;
R⁷, R⁸ represent independently H, substituted or non substituted C₁-C₁₂-alkyl, aryl or R⁷ and R⁸ can form a substituted or non substituted, saturated or non saturated 5 to 7-membered heterocycle including one or more atoms selected in the list consisting of O N and S;
m represents 1, 2, 3 or 4;
as well as a salt; N-oxide; metallic complex, metalloidic complex and/or optically active isomer thereof.

14. A phenyl-amidine derivative of formula (I):

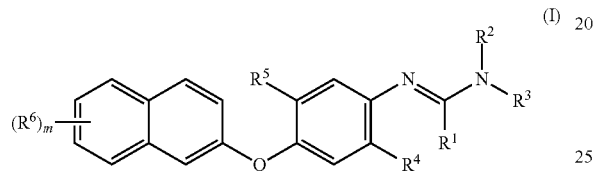

wherein
R¹ represents H;
R² represents a substituted or non substituted C₁-C₁₂-alkyl;
R³ represents a substituted or non substituted C₂-C₁₂-alkyl, substituted or non substituted C₃-C₆-cycloalkyl, substituted or non substituted C₂-C₁₂-alkenyl, substituted or non substituted C₂-C₁₂-alkynyl, halogeno-C₁-C₁₂-alkyl; or
R¹ and R², R¹ and R³ or R² and R³ can form together a substituted or non substituted 5 to 7-membered heterocycle;
R⁴ represents a substituted or non substituted C₁-C₁₂-alkyl, a halogen atom, halogeno-C₁-C₁₂-alkyl, substituted or non substituted O—C₁-C₁₂-alkyl or cyano;
R⁵ represents H, a substituted or non substituted C₁-C₁₂-alkyl, a halogen atom, halogeno-C₁-C₁₂-alkyl, substituted or non substituted O—C₁-C₁₂-alkyl or cyano;
R⁶ represents a substituted or branched C₁-C₁₂-alkyl;
R⁷, R⁸ represent independently H, substituted or non substituted C₁-C₁₂-alkyl, aryl or R⁷ and R⁸ can form a substituted or non substituted, saturated or non saturated 5 to 7-membered heterocycle including one or more atoms selected in the list consisting of O, N and S;
m represents 1, 2, 3 or 4;
as well as a salt; N-oxide; metallic complex, metalloidic complex and/or optically active isomer thereof.

15. A compound of formula (I) according to claim 14 wherein R⁶ represents CH(OH)R⁷ or C(R⁷)=NOR⁸.

16. A phenyl-amidine derivative of formula (I):

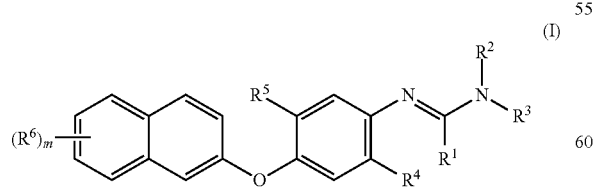

wherein
R¹ represents H;
R² represents a substituted or non substituted C₁-C₁₂-alkyl;
R³ represents a substituted or non substituted C₂-C₁₂-alkyl, substituted or non substituted C₃-C₆-cycloalkyl, substituted or non substituted C₂-C₁₂-alkenyl, substituted or non substituted C₂-C₁₂-alkynyl, halogeno-C₁-C₁₂-alkyl; or
R² and R³ form together a substituted or a non substituted 5 to 7-membered heterocycle;
R⁴ represents a substituted or non substituted C₁-C₁₂-alkyl, a halogen atom, halogeno-C₁-C₁₂-alkyl, substituted or non substituted O—C₁-C₁₂-alkyl or cyano;
R⁵ represents H, a substituted or non substituted C₁-C₁₂-alkyl, a halogen atom, halogeno-C₁-C₁₂-alkyl, substituted or non substituted O—C₁-C₁₂-alkyl or cyano;
R⁶ represents H, halogen, CN, substituted or non substituted phenoxy, substituted or non substituted C₁-C₁₂-alkyl, halogeno-C₁-C₁₂-alkyl, OR⁷, SR⁷, trialkyl-silyl, COR⁷, COOR⁷, C(R⁷)=NOR⁷; NR⁷R⁸, CONR⁷R⁸, SO₂NR⁷R⁸, SONR⁷R⁸;
R⁷, R⁸ represent independently H, substituted or non substituted C₁-C₁₂-alkyl, aryl or R⁷ and R⁸ can form a substituted or non substituted, saturated or non saturated 5 to 7-membered heterocycle including one or more atoms selected in the list consisting of O, N and S;
m represents 1, 2, 3 or 4;
as well as a salt; N-oxide; metallic complex, metalloidic complex and/or optically active isomer thereof.

17. A compound of formula (I) according to claim 16 wherein R² and R³ form together a piperidinyl or a pyrrolidinyl.

18. A compound of formula (I) according to claim 16 wherein R² and R³ form together a 2-alkylated pyrrolidinyl.

19. A compound of formula (I) according to claim 17 wherein
R¹ represents H;
R² and R³ form together piperidinyl;
R⁴ represents methyl;
R⁵ represents methyl; and
R⁶ represents H.

20. A compound of formula (Ia)

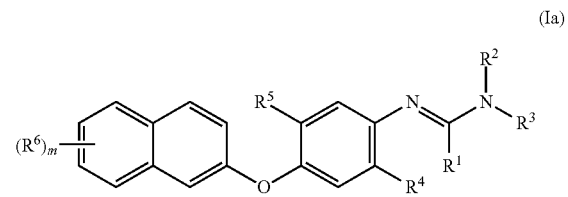

wherein
R¹ represents H;
R² represents C₁-C₁₂-alkyl;
R³ represents C₂-C₁₂-alkyl, C₂-C₁₂-alkenyl or C₃-C₆-cycloalkyl; or
R² and R³ can form together a substituted or non substituted 5 to 7-membered heterocycle;
R⁴ represents C₁-C₁₂-alkyl or a halogen atom;
R⁵ represents a C₁-C₁₂-alkyl or a halogen atom;
R⁶ represents C₁-C₁₂-alkyl; and
m represents 1, 2, 3 or 4;
as well as a salt; N-oxide; metallic complex, metalloidic complex and/or optically active isomer thereof.

21. A phenyl-amidine derivative of formula (I):

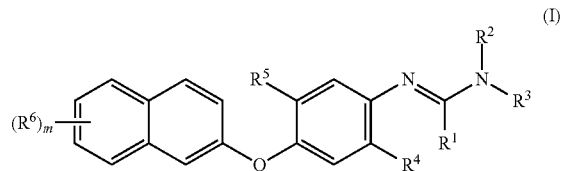

wherein
- $R^1$ represents H;
- $R^2$ represents a substituted or non substituted $C_1$-$C_{12}$-alkyl;
- $R^3$ represents a substituted or non substituted $C_2$-$C_{12}$-alkyl, substituted or non substituted $C_3$-$C_6$-cycloalkyl, substituted or non substituted $C_2$-$C_{12}$-alkenyl, substituted or non substituted $C_2$-$C_{12}$-alkynyl, halogeno-$C_1$-$C_{12}$-alkyl; or
- $R^1$ and $R^2$, $R^1$ and $R^3$ or $R^2$ and $R^3$ can form together a substituted or non substituted 5 to 7-membered heterocycle;
- $R^4$ represents a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;
- $R^5$ represents H, a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;
- $R^6$ represents halogen, CN, substituted or non substituted phenoxy, substituted or non substituted $C_1$-$C_{12}$-alkyl, halogeno-$C_1$-$C_{12}$-alkyl, $OR^7$, $SR^7$, trialkyl-silyl, $COR^7$, $COOR^7$, $C(R^7)$=$NOR^7$; $NR^7R^8$, $CONR^7R^8$, $SO_2NR^7R^8$, $SONR^7R^8$;
- $R^7$, $R^8$ represent independently H, substituted or non substituted $C_1$-$C_{12}$-alkyl, aryl or $R^7$ and $R^8$ can form a substituted or non substituted, saturated or non saturated 5 to 7-membered heterocycle including one or more atoms selected in the list consisting of O, N and S;
- m represents 1, 2, 3 or 4;

as well as a salt; N-oxide; metallic complex, metalloidic complex and/or optically active isomer thereof.

* * * * *